US009423356B2

United States Patent
Ogawa et al.

(10) Patent No.: US 9,423,356 B2
(45) Date of Patent: Aug. 23, 2016

(54) ILLUMINATION APPARATUS AND INSPECTION APPARATUS

(71) Applicants: NuFlare Technology, Inc., Yokohama (JP); Kabushiki Kaisha Toshiba, Minato-ku (JP)

(72) Inventors: Riki Ogawa, Kanagawa (JP); Hiroyuki Nagahama, Saitama (JP); Takeshi Fujiwara, Kanagawa (JP)

(73) Assignees: NuFlare Technology, Inc., Yokohama (JP); Kabushiki Kaisha Toshiba, Minato-ku (JP)

( * ) Notice: Subject to any disclaimer, the term of this patent is extended or adjusted under 35 U.S.C. 154(b) by 195 days.

(21) Appl. No.: 14/228,747

(22) Filed: Mar. 28, 2014

(65) Prior Publication Data

US 2014/0300893 A1    Oct. 9, 2014

(30) Foreign Application Priority Data

Apr. 8, 2013    (JP) .................................. 2013-080796

(51) Int. Cl.
| | |
|---|---|
| G01N 21/88 | (2006.01) |
| G02B 26/10 | (2006.01) |
| G02B 27/09 | (2006.01) |
| G01N 21/956 | (2006.01) |
| G01N 21/95 | (2006.01) |

(52) U.S. Cl.
CPC ........ *G01N 21/8806* (2013.01); *G01N 21/9501* (2013.01); *G01N 21/95607* (2013.01); *G02B 26/10* (2013.01); *G02B 27/0961* (2013.01); *G01N 2021/95676* (2013.01)

(58) Field of Classification Search
None
See application file for complete search history.

(56) References Cited

U.S. PATENT DOCUMENTS

| 4,621,892 A * | 11/1986 | Kataoka ............. G02B 27/0031 359/210.1 |
|---|---|---|
| 4,640,573 A * | 2/1987 | Kataoka ................. G02B 26/10 359/210.1 |
| 6,081,381 A * | 6/2000 | Shalapenok ........... G02B 27/48 359/619 |
| 7,090,359 B2 * | 8/2006 | Kim ......................... G02B 3/06 348/742 |
| 8,023,193 B2 * | 9/2011 | Chen .................. G02B 27/2214 359/621 |

(Continued)

FOREIGN PATENT DOCUMENTS

| JP | 11-72905 | 3/1999 |
|---|---|---|
| JP | 11-072905 A | 3/1999 |
| JP | 2011-95642 | 5/2011 |

*Primary Examiner* — Gordon J Stock, Jr.
(74) *Attorney, Agent, or Firm* — Oblon, McClelland, Maier & Neustadt, L.L.P

(57) ABSTRACT

An illumination apparatus comprising, a light source that emits a laser beam, a lens array on which the laser beam is illuminated, a plurality of element lenses having a diameter greater than or equal to the laser beam are arranged in the lens array, the lens array being rotatable around an optical axis of the laser beam, wherein the two lens arrays are arrayed in an optical axis direction of the laser beam, and the element lenses in each lens array are arranged such that a boundary between the element lenses adjacent to each other radiates from a rotation center of the lens array and a direction in which the element lens of one of the lens arrays traverses the optical axis of the laser beam is orthogonal to a direction in which the element lens of the other lens array traverses the optical axis of the laser beam.

13 Claims, 14 Drawing Sheets

(56) References Cited

U.S. PATENT DOCUMENTS

| | | | | |
|---|---|---|---|---|
| 2005/0140970 A1* | 6/2005 | Vacca | ............... | G01N 21/95607 356/237.2 |
| 2005/0259306 A1* | 11/2005 | Broome | ............. | G02B 26/0875 359/206.1 |
| 2006/0147176 A1* | 7/2006 | Takamatsu | ............. | G02B 21/14 385/147 |
| 2007/0033680 A1* | 2/2007 | Takahashi | .......... | G01N 21/9501 359/362 |
| 2009/0059336 A1* | 3/2009 | Dunphy | ............. | G02B 26/0875 353/33 |
| 2009/0244531 A1* | 10/2009 | Takada | ................. | G01N 21/956 356/237.5 |
| 2010/0321680 A1* | 12/2010 | Takada | ................. | G01N 21/956 356/237.5 |
| 2011/0188734 A1* | 8/2011 | Tsuchiya | ............... | G06T 7/0002 382/149 |

\* cited by examiner

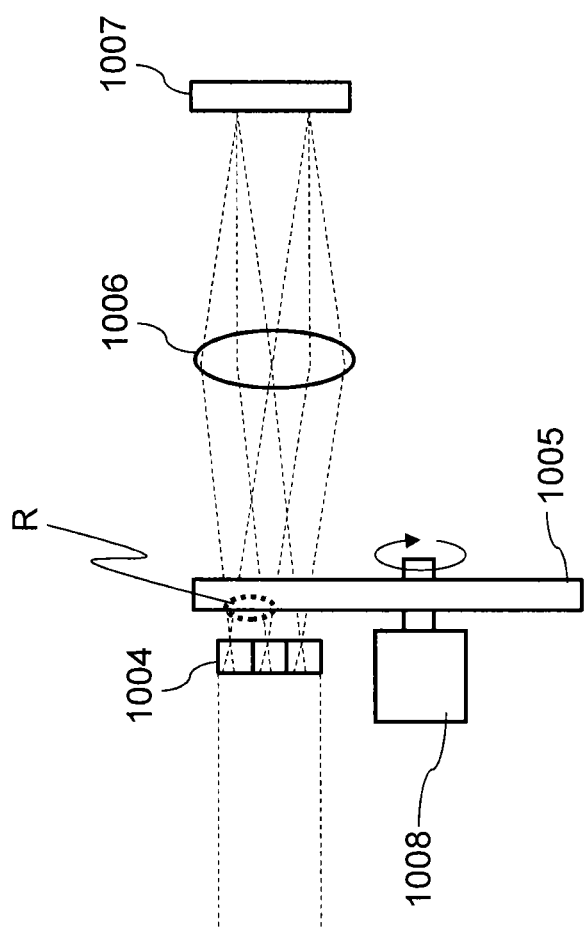

ILLUMINATION APPARATUS AND INSPECTION APPARATUS

CROSS-REFERENCE TO THE RELATED APPLICATION

The entire disclosure of the Japanese Patent Application No. 2013-080796, filed on Apr. 8, 2013 including specification, claims, drawings, and summary, on which the Convention priority of the present application is based, are incorporated herein in its entirety.

FIELD OF THE INVENTION

The present invention relates to an illumination apparatus and inspection Apparatus.

BACKGROUND

With high integration and large capacity of a Large Scale Integration (LSI), a circuit dimension required for a semiconductor element becomes increasingly narrowed. In the semiconductor element, during a production process, an original design pattern (that is, a mask or a reticle, hereinafter collectively referred to as a mask) in which a circuit pattern is formed is exposed and transferred onto a wafer by a reduction projection exposure apparatus called a stepper or a scanner.

It is necessary to improve a production yield of the expensive LSI in a production process. A shape defect of a mask pattern can be cited as a large factor that reduces a production yield of the semiconductor element.

A pattern having a line width of several tens of nanometers is required to be formed in the latest typical logic device. For example, the pattern constituting the LSI has become smaller, from the sub-micrometer order to the nanometer order as typified by a 1-gigabit class DRAM (Dynamic Random Access Memory). As a LCD (Liquid Crystal Display) grows in size with the progress of multimedia, a display with higher resolution capability is required. Specifically, the LCD is enlarged to the size of 500 mm×600 mm or more. On the other hand, the pattern of a TFT (Thin Film Transistor) provided on a liquid crystal substrate becomes smaller.

A shape defect of the mask pattern also becomes smaller according to the above-mentioned situation. Conventionally, fluctuations of various process conditions are absorbed by enhancing dimension accuracy of the mask. Therefore, it is necessary to detect the defect of an extremely small pattern in a mask inspection. Additionally, it is necessary to efficiently inspect a large-area LCD in as quickly as possible.

On the other hand, EUV lithography and Nanoimprint Lithography (NIL) attract attention as a technology for forming the fine pattern. In the EUV lithography, using extreme ultraviolet light as a light source, the pattern can be formed smaller than a conventional exposure apparatus in which ArF light is used. In the nanoimprint lithography, a fine pattern is formed in a resist by pressuring a mold (die) having a nanometer-scale fine structure to the resist on the wafer. In both the EUV lithography and nanoimprint lithography, the pattern formed in the mask and a template, which are of an original plate, is smaller than that of the conventional ArF lithography, and high inspection accuracy is therefore required in the inspection.

Therefore, in the inspection apparatus, a wavelength of illumination light is shortened in order to enhance a resolution capability. For example, deep ultraviolet light having wavelengths of 266 nm or less is used in a laser beam apparatus. However, the light emitted from the laser beam source becomes coherent light, and unfortunately a given interference fringe (speckle) is generated due to coherence.

FIG. 16 is a view illustrating a conventional illumination method.

FIG. 16 shows a lens array 1001 dividing a light beam from a light source (not illustrated) to generate a point light source group. The light becoming the point light source group is shaped into parallel light by a condenser lens 1002, and an object 1003 is illuminated with the parallel light. A position of the lens array 1001 corresponds to a Fourier plane of the object 1003, and a size of the lens array 1001 determines an illumination-side numerical aperture NA. At this point, although a resolution characteristic of an optical system is influenced by the illumination-side numerical aperture NA, generally the illumination-side numerical aperture NA is increased to the same level as a receiving-side numerical aperture NA in order to enhance resolution. Therefore, it is necessary that the point light source group generated by the lens array 1001 have a certain size.

In the optical system shown in FIG. 16, the light transmitted through the element lenses 1001a, 1001b, and 1001c constituting the lens array 1001 overlap one another on the object 1003 with different angles. For this reason, the interference fringe is generated on the object 1003 when the light incident to the element lenses 1001a, 1001b, and 1001c of the lens array 1001 have coherence. The number of point light sources generated by the lens array 1001 generally becomes a number between several hundred to several tens of thousands, and a wavefront of each piece of light is not necessarily an equiphase plane when the light transmitted through the element lenses 1001a, 1001b, and 1001c overlap one another on the object 1003. Therefore, the interference fringe has a random shape. The shape of the interference fringe fluctuates randomly due to an air fluctuation or a mechanical vibration. The randomly fluctuating interference fringe (speckle noise) loses a function of the illumination apparatus that needs to evenly illuminate the object 1003.

A technique has been attempted, in which the light from the light source is transmitted through a flyeye lens and transmitted through a rotating phase plate to eliminate the coherence of the coherent light, thereby reducing the speckle noise.

FIG. 17 is a view illustrating a conventional illumination method in which the rotating phase plate is used. In FIG. 17, the light emitted from the light source (not illustrated) and transmitted through a lens array 1004 is transmitted through a phase plate 1005, and shaped into a parallel light through a condenser lens 1006, and an object 1007 is illuminated with the parallel light. FIG. 18 is an enlarged sectional view of the region R in FIG. 17.

As illustrated in the enlargement shown in FIG. 18, the phase plate 1005 has an irregular shape in a section on the light incident side, and a random arrangement of the irregular shape of the phase plate 1005 provides a phase difference of 0 or π to each of the point light sources. As illustrated in FIG. 17, the interference fringe can be changed at high speed by a structure in which the phase plate 1005 is rotated by a rotating mechanism 1008. The speckle noise remaining in the captured optical image is reduced with increasing shape change of the interference fringe generated within an exposure time of an image sensor (not illustrated) that captures the image of the object 1007.

However, in the conventional illumination method, the speckle noise cannot be reduced beyond a limit defined by a rotating speed of the phase plate and the exposure time of the imaging element. In order to reduce the speckle noise, it is necessary to enhance the rotating speed or lengthen the exposure time of the imaging element. There is a limit to the enhancement of the rotating speed, and the lengthened exposure time leads to a degradation of throughput. Therefore, both these methods are hardly used.

The conventional illumination apparatus has the insufficient resolution capability required in association with the smaller pattern of the semiconductor element, and there is a strong demand to develop the illumination apparatus that can solve the problem and the inspection apparatus provided with the illumination apparatus. An object of the present invention is to provide an illumination apparatus that can reduce the speckle noise more than before. Another object of the present invention is to provide an inspection apparatus that allows detection of fine defect, required in association with the smaller semiconductor element to be performed efficiently in the shortest possible time.

Other challenges and advantages of the present invention are apparent from the following description.

SUMMARY OF THE INVENTION

According to one aspect of the present invention, an illumination apparatus comprising a light source that emits a laser beam, and a lens array on which the laser beam is illuminated, a plurality of element lenses having a diameter greater than or equal to that of the laser beam arranged in the lens array, the lens array being rotatable around an optical axis of the laser beam.

According to another aspect of the present invention, an inspection apparatus comprising an illumination apparatus illuminating a sample in which a pattern of an inspection target is formed with light, an optical image acquiring unit that causes the light transmitted through or reflected from the sample to be illuminated on an image sensor to capture an optical image of the pattern, and a comparison circuit that compares the optical image to a standard image, and determines that pattern is a defect when a difference value between the optical image and the standard image exceeds a predetermined threshold, wherein the illumination apparatus comprises a light source that emits a laser beam, and a lens array on which the laser beam is illuminated, a plurality of element lenses having a diameter greater than or equal to that of the laser beam are arranged in the lens array, the lens array being rotatable around an optical axis of the laser beam.

According to another aspect of the present invention, an inspection apparatus comprises an illumination apparatus illuminating a sample of an inspection target with light, an optical image acquiring unit that causes the light transmitted through or reflected from the sample to be illuminated on an image sensor to capture an optical image of the sample, and a comparison circuit that compares one or a plurality of pixels concerned in the optical image to the surrounding pixels to detect a defect, wherein the illumination apparatus comprises a light source that emits a laser beam, and a lens array on which the laser beam is illuminated, a plurality of element lenses having a diameter greater than or equal to that of the laser beam are arranged in the lens array, the lens array being rotatable around an optical axis of the laser beam.

BRIEF DESCRIPTION OF THE DRAWINGS

FIG. 17 is a view illustrating a conventional illumination method in which the rotating phase plate is used.

FIG. 18 is an enlarged sectional view of a part of the phase plate.

DETAILED DESCRIPTION OF THE EMBODIMENT

Figure 1:
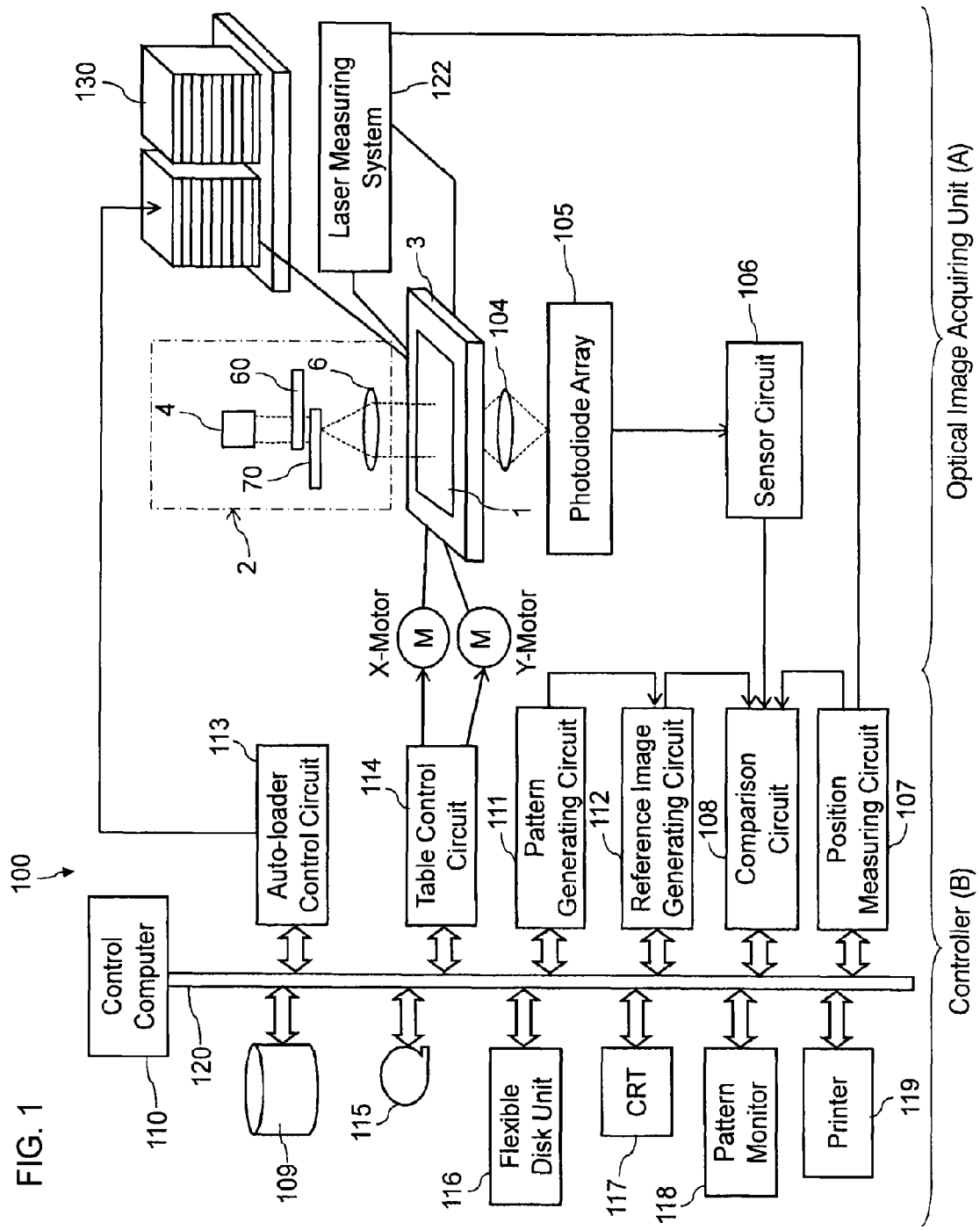
FIG. 1 is a schematic configuration diagram of an inspection apparatus according to the present embodiment.

FIG. 1 is a schematic configuration diagram of an inspection apparatus 100 according to the present embodiment. As illustrated in FIG. 1, an inspection apparatus 100 includes an optical image acquiring unit A and a controller B. In FIG. 1, a configuration unit necessary in the first embodiment is illustrated. However, another well-known configuration unit necessary for an inspection may be used.

An inspection method using the inspection apparatus 100 by a die-to-database method will be described below. In this case, a reference image compared with an optical image to be inspected, is a reference image generated based on design pattern data. However, the inspection apparatus 100 can be applied to the inspection method according to the die-to-die method, and a reference image in this case is an optical image different from the optical image to be inspected.

The optical image acquiring unit includes an illumination apparatus 2, an XY-table 3 that is movable in a horizontal direction (X-direction and Y-direction), an object lens 104, a photodiode array 105, a sensor circuit 106, a laser length measuring system 122, and an auto-loader 130. The mask 101 to be inspected is positioned on the XY-table 3. The XY-table 3 may have a structure that is movable in a rotating direction (θ-direction).

In the controller B, the control computer 110 controlling the whole of the inspection apparatus 100 is connected to a position measuring circuit 107, a comparison circuit 108, a reference image generating circuit 112, an pattern generating circuit 111, an auto-loader controller 113, a table control circuit 114, a magnetic disk drive 109 that is an example of the storage device, a magnetic tape device 115, a flexible disk drive 116, a CRT (Cathode Ray Tube) 117, a pattern monitor 118, and a printer 119 through a bus 120 that constitutes a data transmission line. The XY-table 3 is driven by an X-axis motor and a Y-axis motor under the control of the table control circuit 114. For example, an air slider, a linear motor, and a step motor can be used as these driving mechanisms and can further be used in any combination with each other.

The design pattern data that becomes reference data of the die-to-database method is stored in the magnetic disk drive 109. In the progress of the inspection, the design pattern data is read and transmitted to the pattern generating circuit 111. Then, the image data is transmitted to the reference image generating circuit 112, and used to generate the reference image data.

As illustrated in FIG. 1, the illumination apparatus 2 of the embodiment includes a light source 4 that emits a laser beam, a first lens array 60 and a second lens array 70, which transmit the light emitted from the light source 4, and a condenser lens 6 that shapes the light transmitted through the lens arrays 60 and 70 into parallel light. Deep ultraviolet light having wavelengths of 266 nm or less can be cited as an example of the laser beam.

Figure 4:
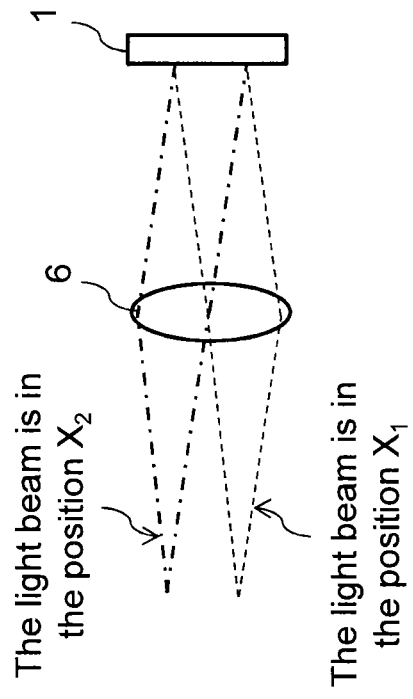
FIG. 4 is a view illustrating an illumination apparatus according to the present embodiment.
Figure 5:
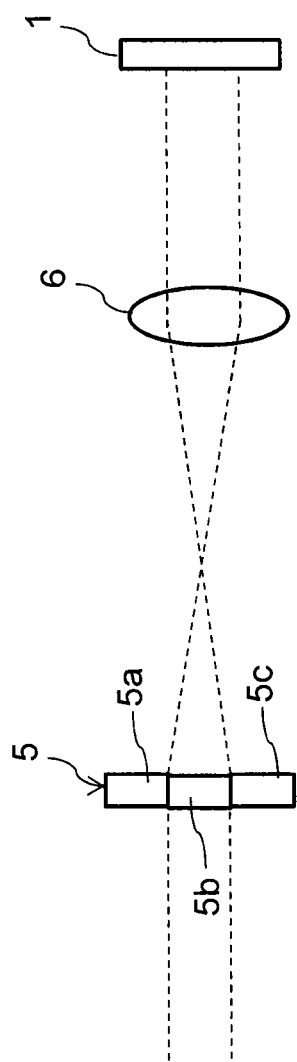
FIG. 5 illustrates the behavior of the light when the sample is scanned using the lens array including the element lens having the diameter equal to that of the incident light.

As illustrated in FIG. 4, the illumination apparatus 2 generates not a point light source group but a single point light source, and scans a certain range at high speed using the generated point light source. According to the present configuration, because of the single point light source, a speckle is not generated on a sample 1. The scan range is set to a range where a necessary numerical aperture NA can be implemented on an illumination side, and designed such that the scan of the scan range ends within an exposure time of an imaging element, thereby obtaining a condition optically equivalent to the case that the point light source group is generated.

Firstly, an example in which the sample is one-dimensionally scanned using the point light source will be described in order to describe the illumination apparatus of the embodiment. In this case, the lens array including an element lens having a diameter greater than or equal to a size (that is, a diameter of incident light, the same applies hereinafter) of the incident light is used. This is because the light, which is emitted from the plurality of point light sources to overlap each other on an object, is prevented from generating an interference fringe.

FIGS. 5 to 8 illustrate a behavior of the light when the sample 1 is scanned using the lens array including the element lens having the diameter equal to that of the incident light.

Figure 6:
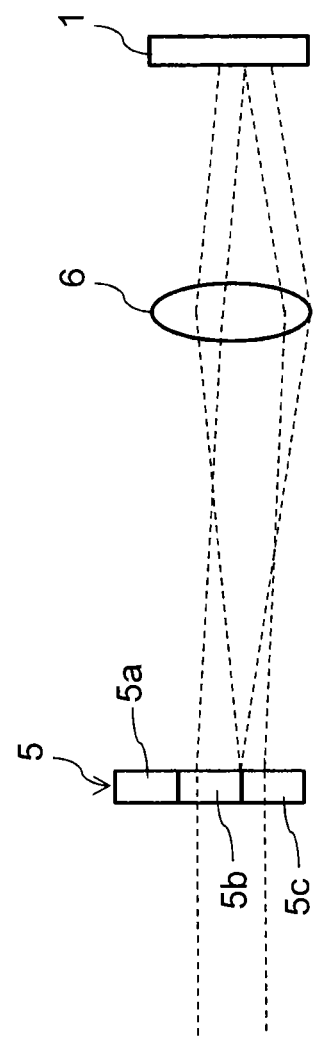
FIG. 6 illustrates the behavior of the light when the sample is scanned using the lens array including the element lens having the diameter equal to that of the incident light.
Figure 7:
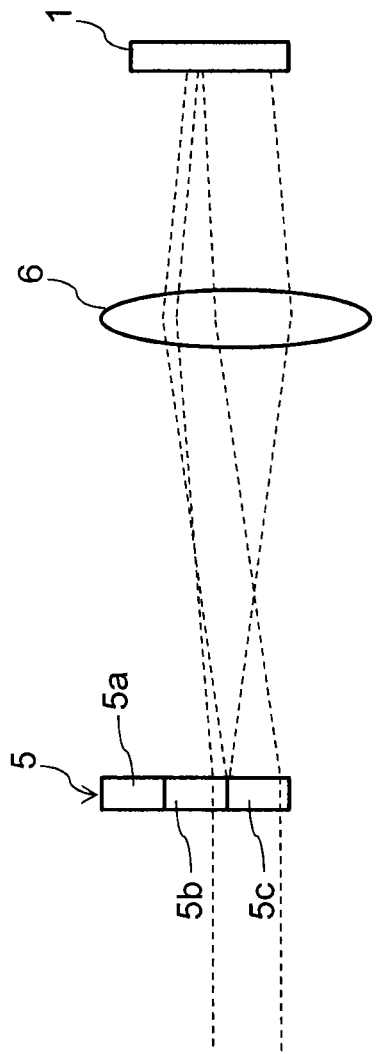
FIG. 7 illustrates the behavior of the light when the sample is scanned using the lens array including the element lens having the diameter equal to that of the incident light.
Figure 8:
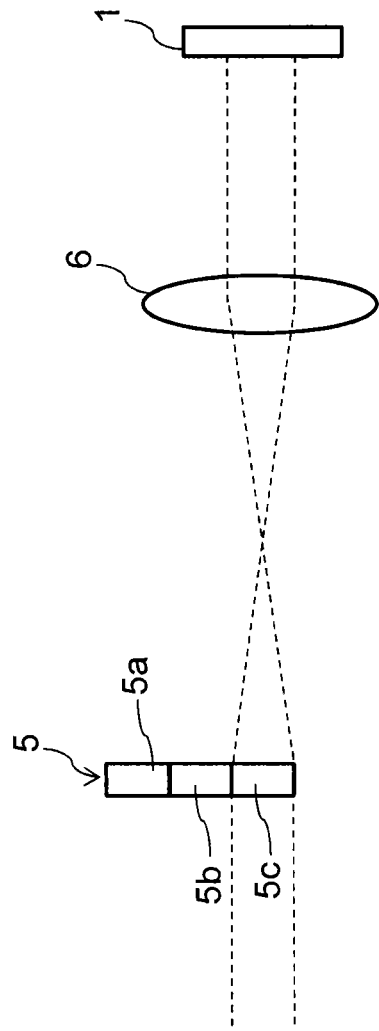
FIG. 8 illustrates the behavior of the light when the sample is scanned using the lens array including the element lens having the diameter equal to that of the incident light.

In FIGS. 5 to 8, each size of element lenses 5a, 5b, and 5c constituting a lens array 5 are equal to the size of the incident light. As illustrated in FIGS. 5 to 8, after the single point light source is shaped into the parallel light by the condenser lens 6, the sample 1 is illuminated with the parallel light. When the scan is performed on the lens array 5 using the point light source, sometimes the incident light straddles the element lenses 5b and 5c as illustrated in FIGS. 6 and 7. Even in such cases, the light transmitted through the element lenses 5b and 5c is separated on the sample 1. That is, the interference fringe is not generated because the light transmitted through the element lens 5b and the light transmitted through the element lens 5c do not overlap each other on the sample 1.

Figure 9:
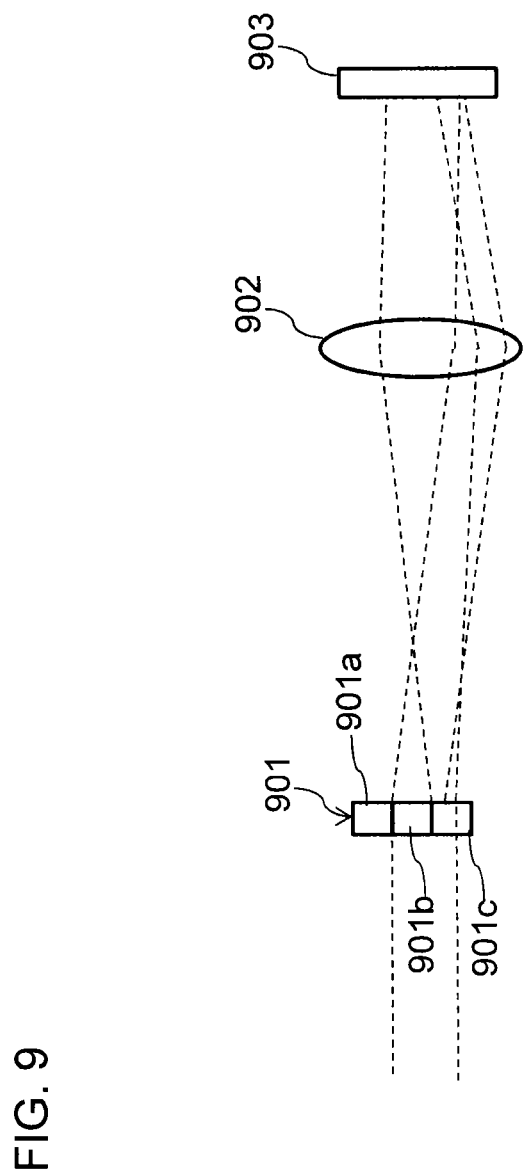
FIG. 9 illustrates a comparative example and the behavior of the light when the sample is scanned using the lens array including the element lens having the diameter smaller than the incident light.

FIG. 9 illustrates a comparative example of the present embodiment. In the comparative example, the sizes of element lenses 901a, 901b, and 901c constituting a lens array 901 are smaller than the size of the incident light. In this case, the light transmitted through the element lenses 901a, 901b, and 901c and shaped into parallel light using a condenser lens 902, and the parallel light overlap each other on an object 903. Therefore, the interference fringe is generated on the object 903. Accordingly, in order not to generate the interference fringe, it is necessary to set the sizes of the element lenses greater than or equal to that of the incident light.

In performing the scan on the lens array 5 using the point light source as illustrated in FIGS. 5 to 8, when a certain element lens is used, for example element lens 5b, a region of the sample 1 illuminated using the element lens deviates continuously from a relative position of a light flux incident to the lens array 5. Therefore, even if the light flux is unevenly incident to the lens array 5, the light flux is smoother as a result of shifting on the sample 1, which allows the sample 1 to be evenly illuminated.

In the illumination apparatus of the embodiment, the illumination-side numerical aperture NA depends on the size of the light flux incident to the lens array 5. Accordingly, in order to increase the illumination-side numerical aperture NA, it is necessary that the diameters of the element lenses 5a, 5b, and 5c be increased while the diameter of the incident light is increased.

For example, the high-speed scan can be performed using the point light source by rotating the lens array. The high-speed scan can also be performed using the point light source by reciprocating motion of the lens array. However, because the scan is stopped at a halfway point from an outward path to an inward path, unevenness is generated in the illumination-side numerical aperture NA or an illumination light quantity on the sample, or a mechanical vibration is generated by the reciprocating motion. Therefore, the rotating motion is more desirable than the reciprocating motion.

Figure 10:
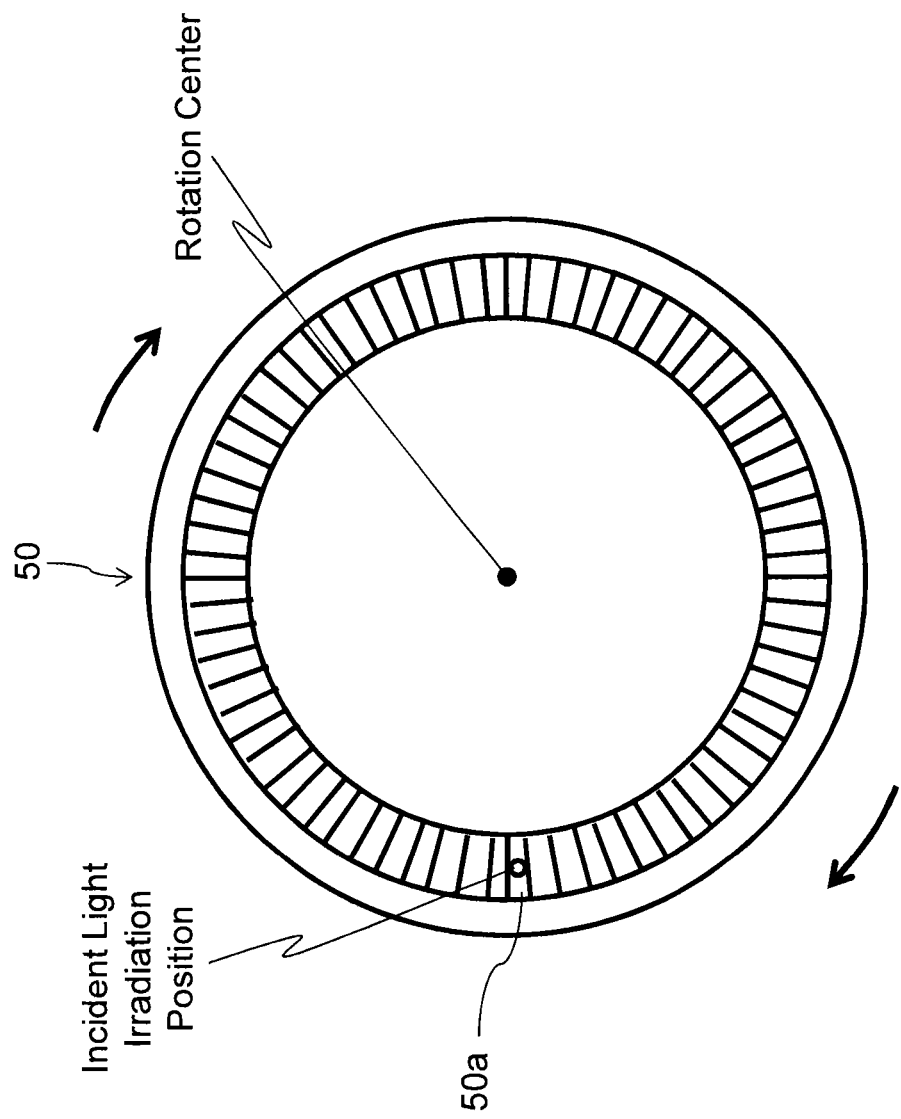
FIG. 10 is a plan view of a rotatable lens array.

FIG. 10 is a plan view of a rotatable lens array. A lens array 50 includes a plurality of cylindrical lenses 50a as the element lenses. Boundaries of the cylindrical lenses 50a are virtually radially arrayed about a rotation center of the lens array 50. A rotating mechanism (not illustrated) is provided in the lens array 50, and the lens array 50 is rotated at a predetermined speed in an arrow direction by the rotating mechanism.

In the lens array 50 in FIG. 10, a distance from the rotation center to an incident light irradiation position is sufficiently increased larger than a width of a cylindrical lens 50a, which allows an opening of the cylindrical lens 50a to be considered to be substantially rectangle.

The illumination apparatus performing the one-dimensional scan can be applied to the inspection apparatus when resolution of an optical image in an X-direction or a Y-direction is not important. An example in which the sample is two-dimensionally scanned using the point light source will be described below.

Figure 11:
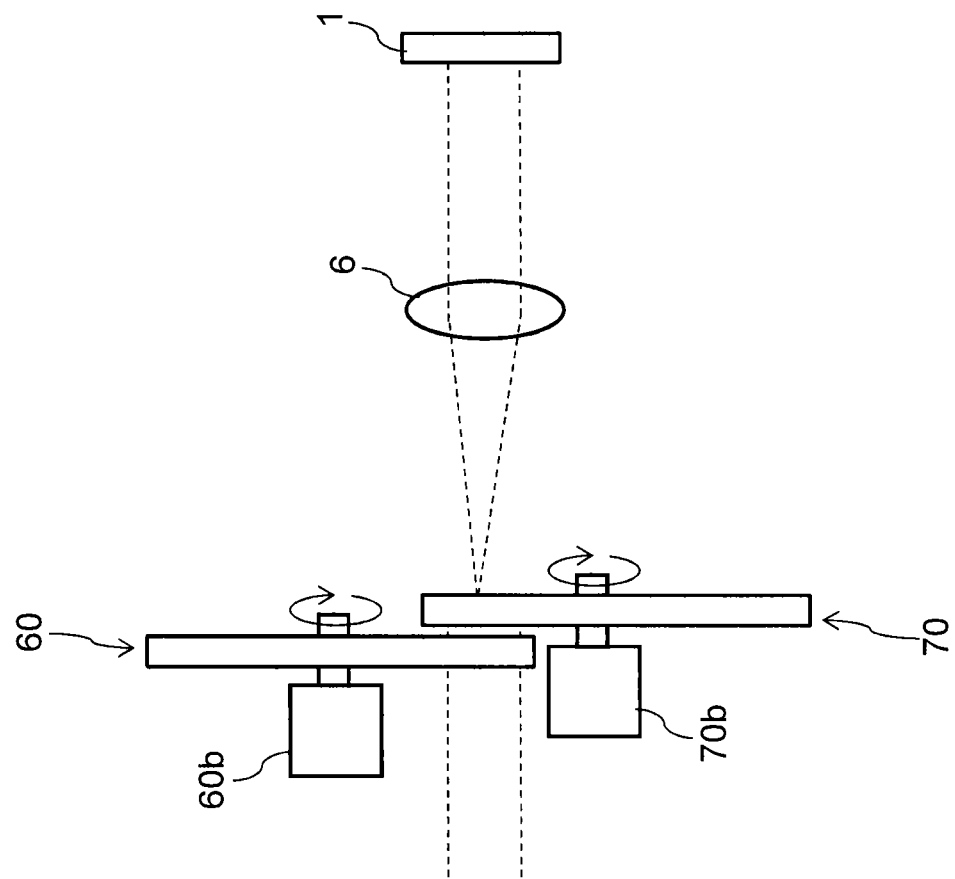
FIG. 11 is an enlarged view illustrating the surrounding area of the lens array of the illumination apparatus in FIG. 1.

As illustrated in FIG. 11, the two-dimensional scan can be performed by arraying the two lens arrays 50 in FIG. 10 in an optical axis direction. FIG. 11 is an enlarged view illustrating the surrounding area of the lens array of the illumination apparatus 2 in FIG. 1.

In FIG. 11, the first lens array 60 is used to scan the sample 1 in the Y-direction using the point light source, and has a structure that is rotatable by a rotating mechanism 60b. On the other hand, the second lens array 70 is used to scan the sample 1 in the X-direction using the point light source, and has a structure that is rotatable in the same direction as the first lens array 60 by a rotating mechanism 70b. After the light transmitted through the first and second lens arrays 60 and 70 is shaped into the parallel light by the condenser lens 6, the sample 1 is illuminated with the parallel light.

Figure 12:
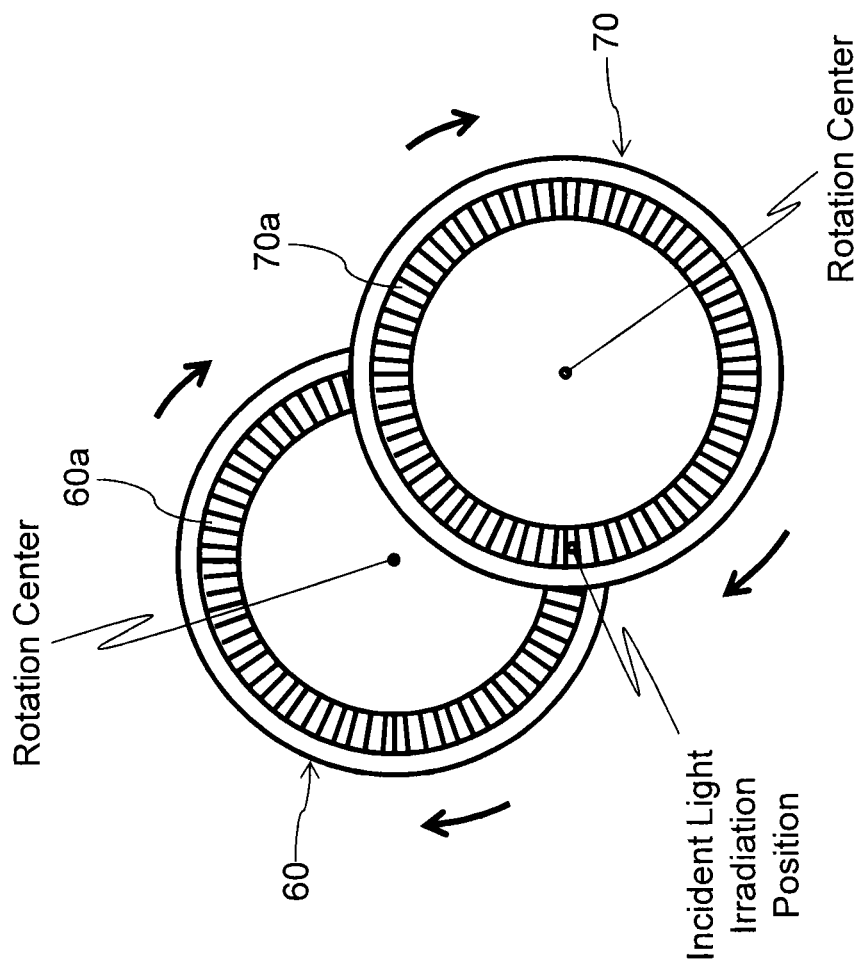
FIG. 12 is a plan view illustrating the first and second lens arrays in FIG. 11 when viewed from the side of the condenser lens.

FIG. 12 is a plan view illustrating the first and second lens arrays 60 and 70 in FIG. 11 when viewed from the side of the condenser lens 6. As illustrated in FIG. 12, the first lens array 60 and the second lens array 70 are arranged such that the boundary drawn by the plurality of cylindrical lenses 60a (in the first lens array 60) and the boundary drawn by the plurality of cylindrical lenses 70a (in the second lens array 70) are orthogonal to each other at the incident light irradiation position. Therefore, a rectangular illumination area can be formed on the sample 1.

By arranging the first lens array 60 and the second lens array 70 as illustrated in FIG. 12, the first lens array 60 is used to scan the sample 1 in the Y-direction at the incident light irradiation position while the second lens array 70 is used to scan the sample 1 in the X-direction. That is, according to scan speeds of the two lens arrays, the sample 1 is two-dimensionally scanned using the point light source formed by the two lens arrays.

As described above, preferably a cylindrical lens is used as each of the element lenses used in the first and second lens arrays 60 and 70. When the two lens arrays have spherical surfaces, light beams are bent by deviations of lens centers of the lens arrays, and an irradiation region fluctuates largely on the sample 1. On the other hand, when the plurality of cylindrical lenses are used in the two lens arrays such that the boundaries formed by the cylindrical lenses arranged in the lens arrays are orthogonal to each other, an influence of the deviation can be eliminated even if the positions of the lens arrays deviate relatively from each other.

In the present embodiment, preferably a rotating speed of one of the two lens arrays is higher than that of the other lens array.

Figure 13:
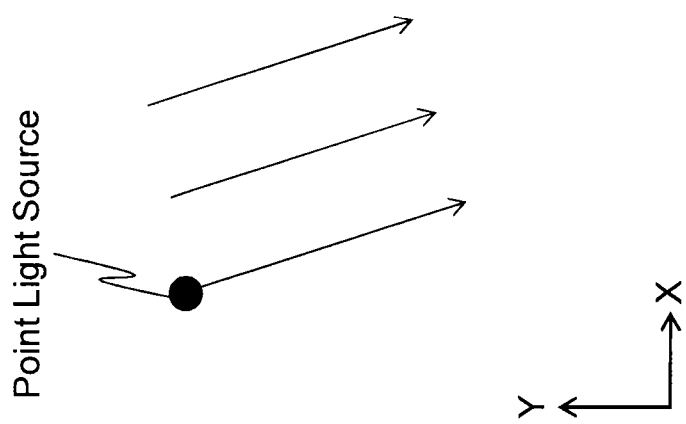
FIG. 13 illustrates the motion of the point light source when the rotating speed of the first lens array used to scan the sample in the Y-direction is set to triple the rotating speed of the second lens array used to scan the sample in the X-direction.

FIG. 13 illustrates the motion of the point light source with the arrows when the rotating speed of the first lens array used to scan the sample in the Y-direction is set to triple the rotating speed of the second lens array used to scan the sample in the X-direction. Actually there are two point light sources because the object is simultaneously illuminated with the light transmitted through the two lens arrays. However, in FIG. 13, only one of the point light sources is shown.

In FIG. 13 as one example, because the first lens array traverses the three element lenses while the second lens array traverses the one element lens, the three element lenses are scanned in the sample using the point light source. The three element lenses are continuously scanned in the sample using the point light source, because the point light source traces the same locus when the second lens array passes through the adjacent element lens.

In order to form the optical image on the sample and obtain a high resolution capability, the scan should be performed with minimal space on the lens array using the point light source. Therefore, it is necessary to increase the number of scan lines of the point light source. At this point, the number of scan lines can be increased by increasing a rotational speed difference between the two lens arrays. However, the number of scan lines is hardly increased by increasing the rotational speed difference.

For example, in FIG. 13, the number of scan lines can be increased when the rotating speed of the second lens array is decreased. However, in this case, because the lens array cannot make one complete rotation within an imaging time, a fluctuation in light quantity or unevenness of the light quantity is generated by the influence of an individual difference between the element lenses constituting the lens array, namely, the influence of a production variation. In order to minimize the influence of the element lens, it is necessary that the time necessary for the slower lens array to make the one complete rotation be matched with the imaging time. As a result, there is a limit in that the speed difference between the first and second lens arrays is realized by decreasing the rotating speed of the second lens array. Furthermore, there is a limit to the increased rotating speed of the first lens array from a structural standpoint.

Figure 14:
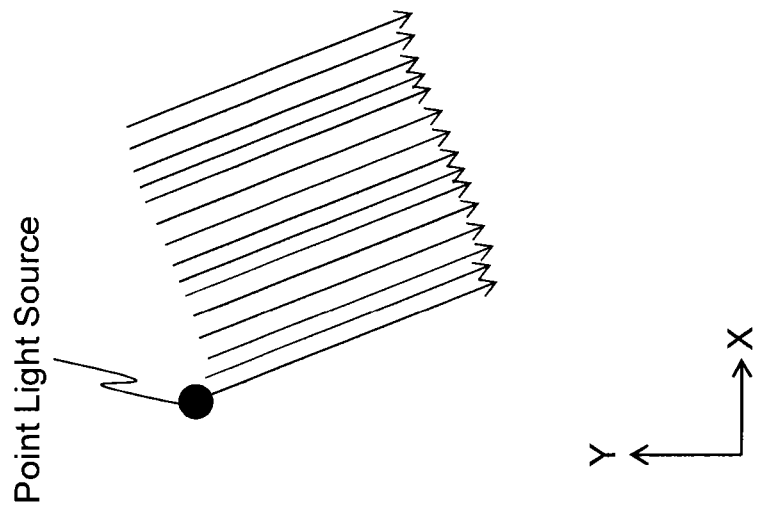
FIG. 14 illustrates the scan positions of the point light source deviated from each other little by little.

Therefore, the speed difference between the first and second lens arrays takes a value except an integral multiple. That is, the speed difference between the first and second lens arrays is adjusted such that the scan positions of the point light source deviate from each other little by little as illustrated in FIG. 14, which allows the number of scan lines to be considerably increased.

According to the illumination apparatus of the embodiment, the point light source is generated using the lens array in which the plurality of element lenses having the size greater than or equal to the diameter of the incident light are used, so that the generation of the interference fringe can be prevented on the sample. Accordingly, unlike the conventional illumination apparatus, the throughput is not degraded by lengthening the exposure time of the imaging element in order to reduce the interference fringe. Even if the unevenness of the light quantity is generated in the incident light, the light quantity is averaged on the sample by performing the scan on the lens array using the point light source. That is, the sample can homogeneously be illuminated.

In the present embodiment, the two lens arrays are rotated while arrayed in the optical axis direction. At this point, the element lenses of each lens array are arranged such that boundaries between the element lenses adjacent to each other are radially arranged from the rotation center of the lens array, and the direction in which element lens of one of the lens arrays traverses the optical axis is orthogonal to the direction in which the element lens of the other lens array traverses the optical axis. Therefore, the scan can be performed in the X-axis direction and the Y-axis direction on the lens array using the point light source. In the present configuration, the necessity of the phase plate of the conventional illumination apparatus is eliminated, so that a low-cost illumination apparatus can be achieved.

In the element lens constituting the lens array, the cylindrical lens is preferable to the spherical lens. The spherical lens has one lens center. When the center of the spherical lens of one of the lens arrays deviates from the center of the spherical lens of the other lens array, an optical path of the transmitted light changes, but the desired region cannot be illuminated on the sample. On the other hand, in the cylindrical lens, the influence can be minimized even if the two lens centers are deviated from each other.

In the case that the cylindrical lens is used as the element lens, it is assumed that the direction in which the lens has a curvature is set to the X-direction while the orthogonal direction, namely, the direction in which the lens has no curvature is set to the Y-direction. When the lens arrays are arranged such that the X-direction having the curvature of the cylindrical lens of one of the lens arrays is orthogonal to the X-direction having the curvature of the cylindrical lens of the other lens array, an action optically similar to that of the spherical lens, namely, the two-dimensional scan can be performed by the cylindrical lenses.

Figure 15:
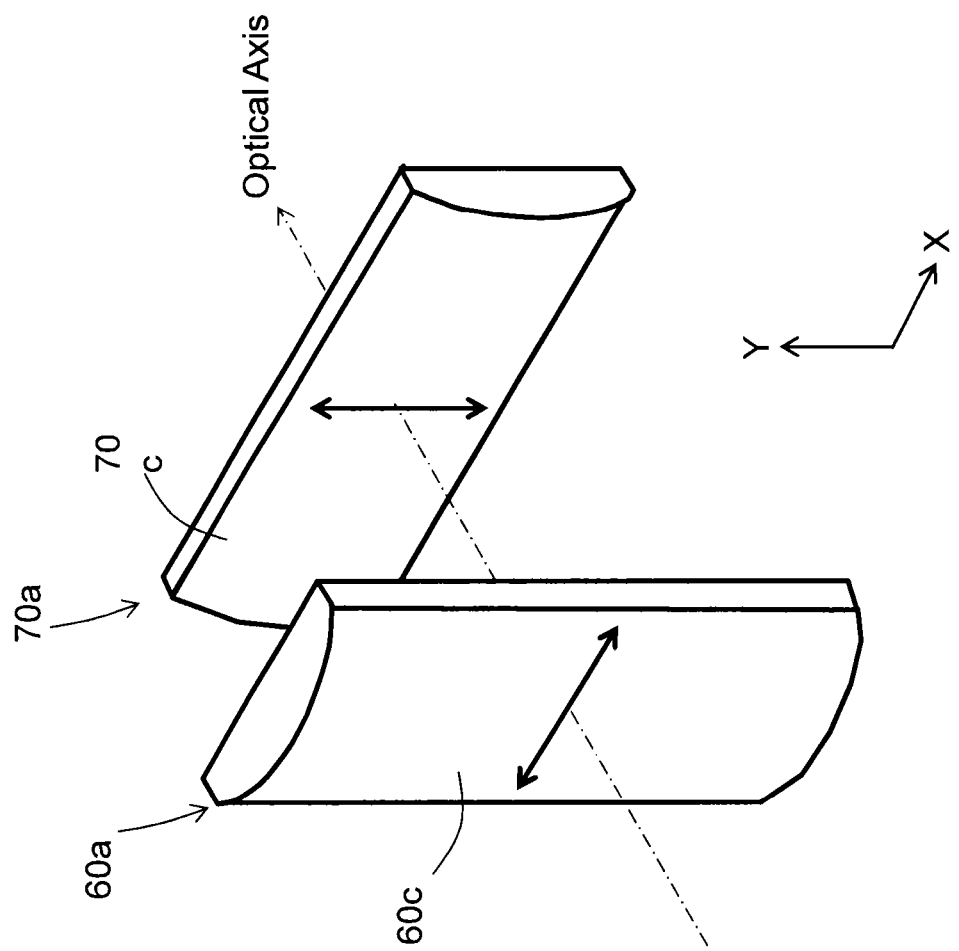
FIG. 15 is a view illustrating an arrangement relationship between the cylindrical lens of the first lens array in FIG. 11 and the cylindrical lens of the second lens array.
Figure 16:
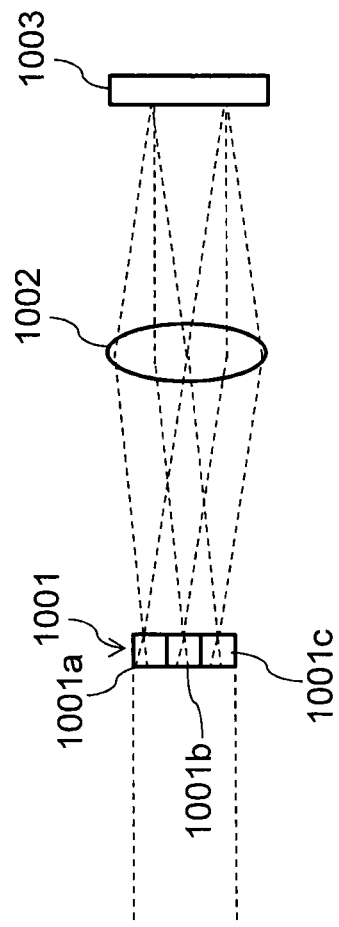
FIG. 16 is a view illustrating a conventional illumination method.

FIG. 15 is a view illustrating an arrangement relationship between the cylindrical lens 60a of the first lens array 60 in FIG. 11 and the cylindrical lens 70a of the second lens array 70. As illustrated in FIG. 15, a light incident area 60c of the cylindrical lens 60a has the curvature in the X-direction. On the other hand, a light incident area 70c of the cylindrical lens 70a has the curvature in the Y-direction. The cylindrical lenses 60a and 70a are arranged such that Y-direction of the cylindrical lens 60a and the X-direction of the cylindrical lens 70a are orthogonal to each other. At this point, the first lens array 60 is rotated in the X-direction and the second lens array 70 is rotated in the Y-direction.

In the illumination apparatus of the embodiment, the changes in rotating speeds of the two lens arrays can increase the number of scan lines of the point light source on the lens array to improve an image forming characteristic on the sample. In this case, the speed difference between the two lens arrays is set to the value except the integral multiple, so that the number of scan lines can significantly be increased compared with the integral multiple. However, the time necessary for the lens array having the slower rotating speed to make the one completion rotation is matched with the imaging time of the image sensor that captures the optical image of the sample.

An example of a method for inspecting the sample 1 with the inspection apparatus 100 in FIG. 1 will be described below.

The inspection process includes a process of acquiring the optical image of the sample 1 (optical image acquiring process), a process of storing the design pattern data of the pattern formed in the sample 1 (Store the Design Pattern data), an pattern generating process and a filtering process, that is, an example of the process of generating the reference image, and a process of comparing the optical image to the reference image.

(Optical Image Acquiring Process)

In the optical image acquiring process, the optical image acquiring unit A in FIG. 1 acquires the optical image (measured data) of the sample 1. At this point, the optical image is the image of the sample 1 in which a graphic is drawn based on graphic data included in design pattern data. Examples of the sample 1 include a mask used in photolithography technology and a template used in a nanoimprint technology. An example of a specific method for acquiring the optical image will be described with reference to FIG. 1.

The sample 1 is placed on the XY-table 3. The XY-table 3 is driven by the table control circuit 114 under the control of the table control circuit 114, and is movable by an X-axis motor and a Y-axis motor comprising driving mechanisms that drives in an X-direction and a Y-direction. For example, an air slider, a linear motor, and a step motor can be used as these driving mechanisms and can further be used in any combination with each other. The movement position of the XY-table 3 is measured by the laser length measuring system 122 and transmitted to the position measuring circuit 107. The sample 1 on the XY-table 3 is automatically conveyed from the autoloader 130 that is driven by the autoloader control circuit 113, and automatically discharged after the inspection.

The illumination apparatus 2 is the illumination apparatus of the embodiment described above, and irradiates the sample 1 with defect inspection light. The light transmitted through the sample 1 forms the optical image on the photodiode array 105 through the objective lens 104.

Figure 3:
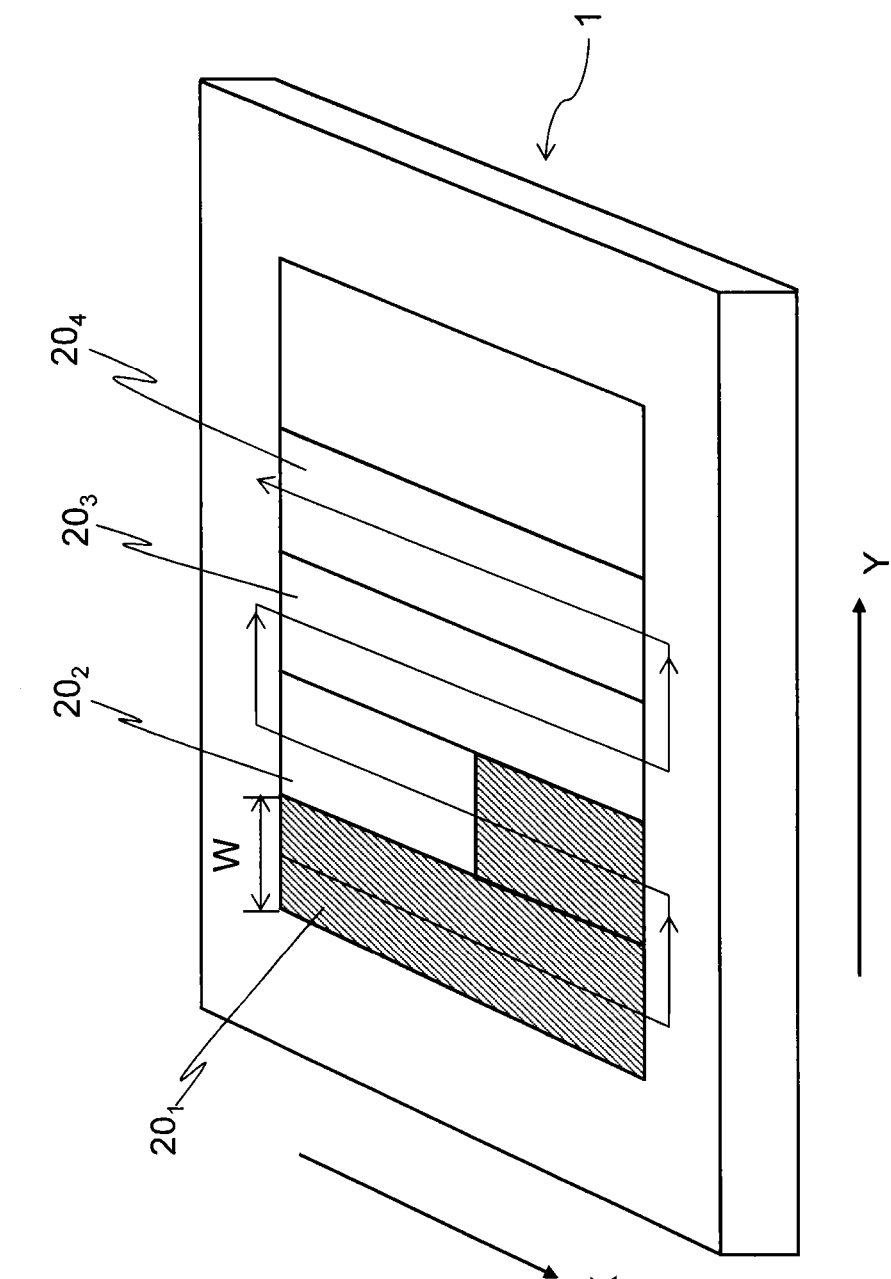
FIG. 3 is a view illustrating a procedure for acquiring an optical image for the detection of the defect of the pattern formed in the sample.

FIG. 3 is a view illustrating a procedure for acquiring an optical image for the detection of the defect of the pattern formed in the sample 1.

In FIG. 3, it is assumed that the sample 1 is positioned on the XY-table 3 in FIG. 1. The inspection region in the sample 1 is virtually divided into the strip-shaped multiple inspection regions, namely, stripes $20_1, 20_2, 20_3, 20_4, \ldots$ as illustrated in FIG. 3. For example, each stripe is a region having the width of several hundred micrometers and the length of about 100 mm corresponding to the total length in the X-direction or the Y-direction of the sample 1.

The optical image is acquired in each stripe. That is, in acquiring the optical image in FIG. 3, the operation of the XY-table 3 is controlled such that the each stripe $20_1, 20_2, 20_3, 20_4, \ldots$ is continuously scanned. Specifically, the optical image of the sample 1 is acquired while the XY-table 3 moved in the –X-direction of FIG. 3. The image having a scan width W in FIG. 3 is continuously input to the photodiode array 105 in FIG. 1. That is, the image of the second stripe $20_2$ is acquired after the image of the first stripe $20_1$ is acquired. In this case, after the XY-table 3 moves in the –Y-direction in a stepwise manner, the optical image is acquired while the XY-table 3 moves in the direction (X-direction) opposite to the direction (–X-direction) in which the image of the first stripe $20_1$ is acquired, and the image having the scan width W is continuously input to the photodiode array 105. In the case that the image of the third stripe $20_3$ is acquired, after moving in the –Y-direction in the stepwise manner, the XY-table 3 moves in the direction opposite to the direction (X-direction) in which the image of the second stripe $20_2$ is acquired, namely, the direction (–X-direction) in which the image of the first stripe $20_1$ is acquired. An arrow in FIG. 3 indicates the optical image acquiring direction and sequence, and a hatched portion indicates the region where the optical image is already acquired.

The photodiode array 105 performs the photoelectric conversion to the pattern image formed on the photodiode array 105 in FIG. 1, and the sensor circuit 106 performs the A/D (analog-digital) conversion to the pattern image. Image sensors are arranged in the photodiode array 105. As for the image sensors according to the present embodiment, a line sensor, in which CCD cameras as imaging devices are arranged in a row, can be used, as one example. The line sensor includes a TDI (Time Delay Integration) sensor. A pattern of the sample 1 is imaged by the TDI sensor while the XY-table 3 continuously moves in the X-axis direction.

The optical image thus acquired is sent to the comparison circuit 108 of FIG. 1.

Figure 2:
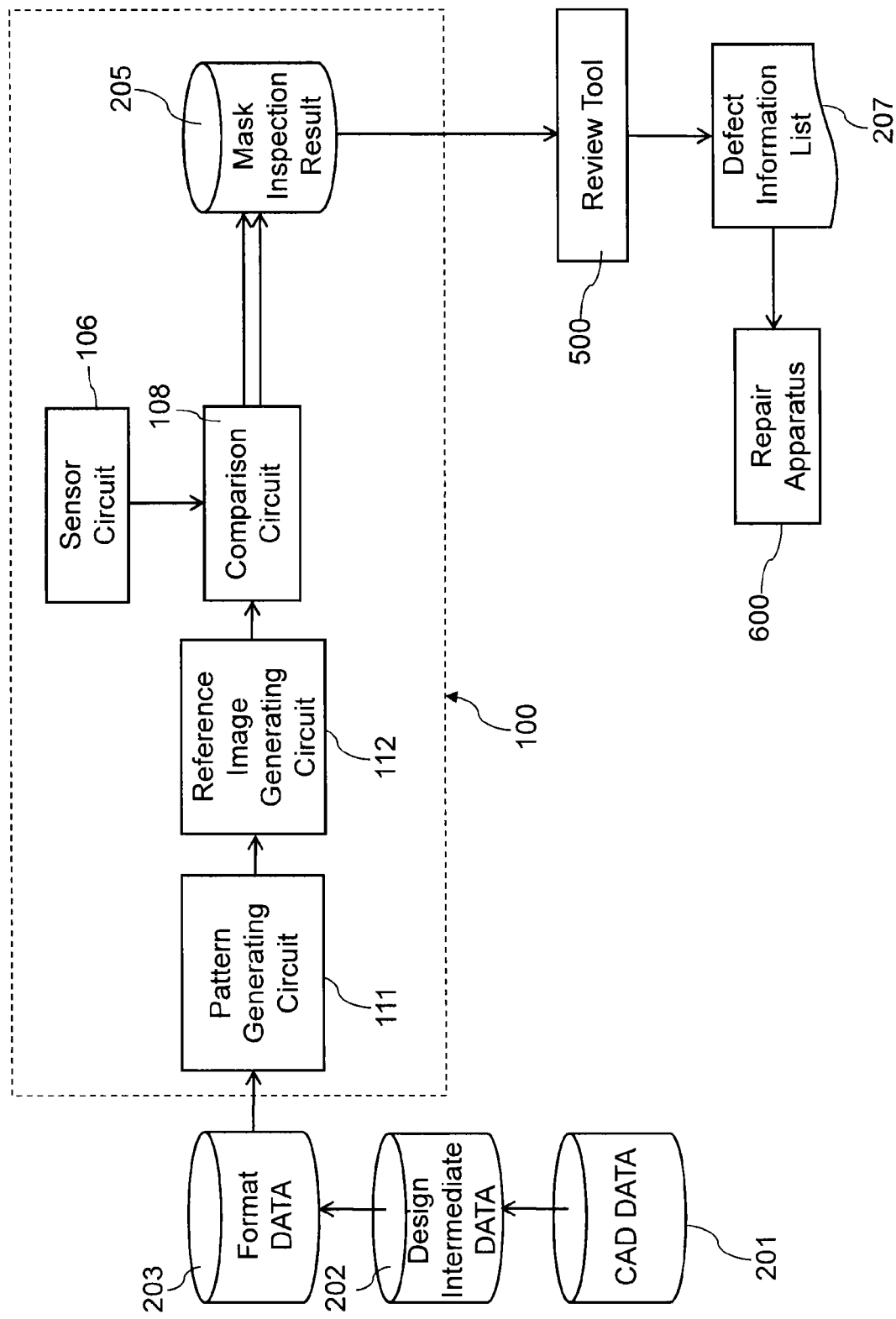
FIG. 2 is a view illustrating a data flow in the inspection apparatus of FIG. 1.

FIG. 2 is a view illustrating a data flow in the inspection apparatus 100 of FIG. 1.

As illustrated in FIG. 2, CAD data 201 produced by a designer (user) is converted into design intermediate data 202 having a hierarchical format. The design pattern data, which is produced in each layer and formed in the sample 1, is stored in the design intermediate data 202. At this point, generally the inspection apparatus is configured not to directly read the design intermediate data 202. That is, independent format data is used by each manufacturer of an inspection apparatus. For this reason, the design intermediate data 202 is input to the inspection apparatus 100 after conversion into format data 203 unique to the inspection apparatus in each layer. In this case, the format data 203 can be set to a data format that is unique to the inspection apparatus 100.

(Storing Process)

The design pattern data that was used to form the pattern on the mask 1 is stored in the magnetic disk unit 109 in FIG. 1 that is an example of the storage device.

The figure patterns included in the design pattern may be a rectangle or a triangle as a basic graphic pattern. For example, Graphic data in which the shape, size, and position of each figure pattern is stored in the magnetic disk drive 109. For example, the graphic data is information such as a coordinate (x, y) from the original position of the graphic pattern, a side length, and a figure code that becomes an identifier identifying a figure pattern type such as a rectangle and a triangle.

A set of graphic patterns existing within a range of several tens of micrometers is generally called a cluster or a cell, and the data is layered using the cluster or cell. In the cluster or cell, a disposition coordinate and a repetitive amount are defined in the case that various graphic patterns are separately disposed or repetitively disposed with a certain distance. The cluster or cell data is disposed in a flame. The flame has, for example, a width of several hundred micrometers and a length of about 100 mm that corresponds to a total length in an X-direction or a Y-direction of the sample 1.

(Pattern Generating Process)

At the pattern generating process, the pattern generating circuit 111 shown in FIG. 1 reads design pattern data of the sample 1 from the first magnetic disk unit 109 through the control computer 110 and converts it into 2-bit or other multiple-bit image data (bit pattern data). This image data is sent to the reference image generating circuit 112.

Specifically, upon reading the design pattern data (serving as feature data), the pattern generating circuit 111 expands it to produce data of each pattern feature, and interprets the shape code in the data indicative of the shape of the pattern feature and obtains its dimensions. The pattern generating circuit 111 then divides the pattern into an imaginary grid of squares (or grid elements) having predetermined quantization dimensions, and produces 2-bit or other multiple-bit design image data of the design pattern segment in each grid element. By using the produced design image data, the pattern generating circuit 111 calculates the design pattern occupancy in each grid element (corresponding to a sensor pixel). This pattern occupancy in each pixel represents the pixel value.

(Filtering Process)

In the filtering process, the reference image generating circuit 112 in FIG. 1 performs the proper filtering to the design pattern data, that is, the graphic image data. The reason is as follows. The optical image (or the measurement data representing it) output from the sensor circuit 106 in FIG. 1 is somewhat "blurred" due to the resolution characteristics of the object lens 104 and due to the aperture effect in the photodiode array 105, that is, this optical image is a spatially low-pass filtered image. Therefore, since the design image data corresponding to the optical image is digital data consisting of digital values representing the intensity (or gray scale) of each point of the image, this design image data may be filtered to match the "blurred" optical image, or measurement data. In this way, a reference image to be compared with the optical image is produced.

(Comparing Process)

The optical image data from the sensor circuit 106 is sent to the comparison circuit 108, as described above. The design pattern data, on the other hand, is converted into the reference image data by the pattern generating circuit 111 and the reference image generating circuit 112, and then also sent to the comparison circuit 108.

The comparison circuit 108 compares each portion of the optical image received from the sensor circuit 106 with the corresponding portion of the reference image generated by the reference image generating circuit 112 in accordance with a suitable comparison determination algorithm.

The defect determination can be made by the following two methods. One of the methods is the method for determining that the inspection target is the defect in the case that the difference exceeding a predetermined threshold is recognized between the position of a contour in the reference image and the position of a contour in the optical image. The other method is the method for determining that the inspection target is the defect in the case that the ratio of the pattern line width in the reference image and the pattern line width in the optical image exceeds a predetermined threshold. In this method, the ratio of the inter-pattern distance in the reference image and the inter-pattern distance in the optical image may be used.

As the result of the comparison, when a difference between the optical image data and the reference image data exceeds a predetermined value, the corresponding portion is determined as a defect. Subsequently, the coordinates of the defect and the optical image and the reference image as a basis for the defect determination are stored in the magnetic disk unit 109. The data that is stored, corresponds to the mask inspection result 205 in FIG. 2.

The mask inspection result 205 is transmitted to a review tool 500 as illustrated in FIG. 2. A review process is an operation in which the operator determines whether the detected defect will become a practical problem. Specifically, the operator visually determines whether the defect needs to be corrected by comparing the reference image that is the basis of the defect determination to the optical image including the defect.

In the review apparatus 500, an image at the defect portion of the sample 1 is displayed while a table on which the sample 1 is placed is moved so that the defect coordinates of defects can be observed one by one. At the same time, judgment of the defect determination, and reference image data and optical image data used as a basis for the determination are arranged and displayed on the screen of the computer of the review apparatus 500 so that judgment, the optical image and the reference image can be confirmed.

When the inspection apparatus 100 is equipped with the review apparatus 500, the image of the defect portion of the sample 1 is displayed using an observation optical system of the inspection apparatus 100. At the same time, the optical image and the reference image as the determination conditions of the defect determination and the basis of the defect determination are displayed using the screen of the control computer 110 illustrated in FIG. 1.

The defect information discriminated through the review process is stored in the magnetic disk device 109 of FIG. 1. In FIG. 2, when at least one defect to be modified is confirmed in the review apparatus 500, the sample 1 is sent with a defect information list 207 to a repair apparatus 600 as an exterior apparatus of the inspection apparatus 100. Since a modification method is different depending on whether the type of the defect is a protrusion-type defect or a recess-type defect, the types of the defect including the distinction between the protrusion type and the recess type and the coordinates of the defect are attached to the defect information list 207.

The inspection apparatus of the embodiment includes the illumination apparatus in which the speckle noise can be reduced more than before while the laser beam is used as the light source. Accordingly, in the inspection apparatus, detection of fine defects, required in association with the finer semiconductor element can efficiently be performed in a shorter time.

The present invention is not limited to the present embodiment, but various modifications can be made without departing from the scope of the invention. For example, in the inspection apparatus 100 in FIG. 1, the illumination apparatus 2 may be arranged below the sample 1 to form an image of the light reflected by the sample 1 on the photodiode array 105 using the objective lens 104.

The above description of the present embodiment has not specified apparatus constructions, control methods, etc., which are not essential to the description of the invention, since any suitable apparatus construction, control methods, etc. can be employed to implement the invention. Further, the scope of this invention encompasses all support apparatuses employing the elements of the invention and variations thereof, which can be designed by those skilled in the art.

Further the present invention is not limited to die-to-database inspection method and die-to-die inspection method. For example, the present invention can be also applied to the case for comparing the pixel concerned to surrounding pixels in one image such as an inspection for template of nanoimprint lithography technique.

More particularly, either the die-to-database method or the die-to-die method may be used to inspect the pattern finer than the optical resolution limit. On the other hand, a method for comparing the pixel concerned in one image to surrounding pixels can also be used to inspect the pattern larger than the optical resolution limit.

In the method for comparing the one pixel or plurality of concerned pixels to the surrounding pixels, the defect can be detected even in the optical image having the repetitive pattern finer than the resolution limit of the optical system. For example, in the case that a hole pattern having a hole diameter smaller than the resolution limit of the observation optical system is formed on the sample, a shape defect caused by edge roughness and a lack of pattern generates a disorder of the pattern, and a gradation value at a point where the shape defect exists differs from surrounding gradation values. On the other hand, in the case that the regular pattern is repeated without any shape defect, the gradation values of the optical image are equalized.

Accordingly, an evaluation region of the sample is divided into predetermined unit regions to check the variation in gradation value in each unit region, which allows the detection of the shape defect caused by the edge roughness and the lack of pattern. For example, the predetermined unit region may be set to the region of 1 mm×1 mm.

The change of the gradation value is also observed in the shape defect due to the abnormal hole diameter of the pattern or the abnormal void between the patterns adjacent to each other due to the position deviation.

In this case, the shape defect due to the abnormal hole diameter of the pattern or the abnormal void between the patterns adjacent to each other due to the position deviation can be detected by comparing average gradation values of the unit regions to each other.

When the hole diameters and the voids are uniformly formed, the average gradation values of the unit regions become uniform. On the other hand, for example, when some of the hole diameters are decreased, there is a difference between the average gradation value of the unit region where the abnormal hole diameter is formed and the average gradation value of the unit region where the normal hole diameter is formed. In the case that the position of the pattern deviates to generate the fluctuation in distance between the patterns, there is also a difference between the average gradation value of the unit region and the average gradation value of another unit region.

Accordingly, the evaluation region is divided into the predetermined unit regions to compare the average gradation values of the unit regions to each other, which allows the abnormal line width or the abnormal void to be detected in the pattern having the dimensions smaller than the resolution limit of the observation optical system.

In the present embodiment, for example, the comparison circuit 108 can compare the one pixel, or a sum or average of a plurality of pixels concerned in the optical image to the surrounding pixels to detect a defect.

As described above, the features of the present invention may be summarized as follows.

According to one aspect of the present invention, an illumination apparatus comprises a light source that emits a laser beam, and a lens array on which the laser beam is illuminated, a plurality of element lenses having a diameter greater than or equal to that of the laser beam are arranged in the lens array, the lens array being rotatable around an optical axis of the laser beam.

Further to this aspect of the present invention, the illumination apparatus, wherein the two lens arrays are arrayed in an optical axis direction of the laser beam, and the element lenses in each lens array are arranged such that a boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

Further to this aspect of the present invention, the illumination apparatus wherein the element lens is a cylindrical lens, wherein a direction, in which an incident area of the laser beam has a curvature in the cylindrical lens of one of the lens arrays, is orthogonal to a direction in which an incident area of the laser beam has curvature in the cylindrical lens of the other lens array, and one of the lens arrays is rotated in a direction in which the incident area of the cylindrical lens thereof has the curvature, and the other lens array is also rotated in a direction in which the incident area of the cylindrical lens thereof has the curvature.

Further to this aspect of the present invention, the illumination apparatus, wherein the two lens arrays differ from each other in a rotating speed.

Further to this aspect of the present invention, the illumination apparatus, wherein the rotating speed of one of the two lens arrays is not an integral multiple of the rotating speed of the other lens array.

According to other aspect of the present invention, an inspection apparatus comprises an illumination apparatus illuminating a sample in which a pattern of an inspection target is formed with light, an optical image acquiring unit that causes the light transmitted through or reflected from the sample to be illuminated on an image sensor to capture an optical image of the pattern, and a comparison circuit that compares the optical image to a standard image, and determines that pattern is a defect when a difference value between the optical image and the standard image exceeds a predetermined threshold. The illumination apparatus comprises a light source that emits a laser beam, and a lens array on which the laser beam is illuminated, a plurality of element lenses having a diameter greater than or equal to that of the laser beam are arranged in the lens array, the lens array being rotatable around an optical axis of the laser beam.

Further to this aspect of the present invention, the illumination apparatus, wherein the two lens arrays are arrayed in an optical axis direction of the laser beam, and the element lenses in each lens array are arranged such that boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

Further to this aspect of the present invention, the illumination apparatus, wherein the element lens is a cylindrical lens, a direction in which an incident area of the laser beam has a curvature in the cylindrical lens of one of the lens arrays is orthogonal to a direction in which an incident area of the laser beam has curvature in the cylindrical lens of the other lens array, one of the lens arrays is rotated in a direction in which the incident area of the cylindrical lens thereof has the curvature, and the other lens array is also rotated in a direction in which the incident area of the cylindrical lens thereof has the curvature.

Further to this aspect of the present invention, the inspection apparatus, wherein the two lens arrays differ from each other in a rotating speed, and a time necessary for the lens array having the slower rotating speed to make one completion rotation is matched with an imaging time of the image sensor.

Further to this aspect of the present invention, the illumination apparatus, wherein the rotating speed of one of the two lens arrays is not an integral multiple of the rotating speed of the other lens array.

Further to this aspect of the present invention, the inspection apparatus, wherein the standard image is a reference image produced from design data of the pattern.

According to other aspect of the present invention, an inspection apparatus comprises an illumination apparatus illuminating a sample of an inspection target with light, an optical image acquiring unit that causes the light transmitted through or reflected from the sample to be illuminated on an image sensor to capture an optical image of the sample, and a comparison circuit that compares one or a plurality of pixels concerned in the optical image to the surrounding pixels to detect a defect. The illumination apparatus comprises a light source that emits a laser beam, and a lens array on which the laser beam is illuminated, a plurality of element lenses having a diameter greater than or equal to that of the laser beam are arranged in the lens array, the lens array being rotatable around an optical axis of the laser beam.

Further to this aspect of the present invention, the illumination apparatus, wherein the two lens arrays are arrayed in an optical axis direction of the laser beam, and the element lenses in each lens array are arranged such that boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

Further to this aspect of the present invention, the illumination apparatus, wherein the element lens is a cylindrical lens, a direction in which an incident area of the laser beam has a curvature in the cylindrical lens of one of the lens arrays is orthogonal to a direction in which an incident area of the laser beam has no curvature in the cylindrical lens of the other lens array, one of the lens arrays is rotated in a direction in which the incident area of the cylindrical lens thereof has the curvature, and the other lens array is also rotated in a direction in which the incident area of the cylindrical lens thereof has the curvature.

Further to this aspect of the present invention, the inspection apparatus, wherein the two lens arrays differ from each other in a rotating speed, and a time necessary for the lens array having the slower rotating speed to make one completion rotation is matched with an imaging time of the image sensor.

Further to this aspect of the present invention, the illumination apparatus, wherein the rotating speed of one of the two lens arrays is not an integral multiple of the rotating speed of the other lens array.

What is claimed is:

1. An illumination apparatus comprising:
a light source that emits a laser beam; and
two lens arrays to which the laser beam is illuminated,
a plurality of element lenses, each element lens having a diameter greater than or equal to that of the laser beam, arranged in the lens arrays, the lens arrays being rotatable through an optical axis of the laser beam,
wherein the two lens arrays are arrayed in an optical axis direction of the laser beam, and
the element lenses in each lens array are arranged such that a boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

2. The illumination apparatus according to claim 1, wherein each of the element lenses are a cylindrical lens, wherein
a direction, in which an incident area of the laser beam has a curvature in the cylindrical lens of one of the lens arrays, is orthogonal to a direction in which an incident area of the laser beam has curvature in the cylindrical lens of the other lens array, and
one of the lens arrays is rotated in a direction in which the incident area of the cylindrical lens thereof has the curvature, and
the other lens array is also rotated in a direction in which the incident area of the cylindrical lens thereof has the curvature.

3. The illumination apparatus according to claim 1, wherein the two lens arrays differ from each other in a rotating speed.

4. The illumination apparatus according to claim 3, wherein the rotating speed of one of the two lens arrays is not an integral multiple of the rotating speed of the other lens array.

5. An inspection apparatus comprising:
an illumination apparatus for illuminating a sample, in which a pattern of an inspection target is formed with light, comprising of a light source that emits a laser beam, and two lens arrays to which the laser beam is illuminated, a plurality of element lenses, each element lens having a diameter greater than or equal to that of the laser beam, arranged in the lens arrays, the lens arrays being rotatable through an optical axis of the laser beam;
an optical image acquiring unit that causes the light transmitted through the sample to be illuminated on an image sensor to acquire an optical image of the pattern; and
a comparison circuit that compares the optical image to a standard image, and determines that pattern is a defect when a difference value between the optical image and the standard image exceeds a predetermined threshold;
wherein the two lens arrays are arrayed in an optical axis direction of the laser beam, and
the element lenses in each lens array are arranged such that boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

6. The inspection apparatus according to claim 5, wherein each of the element lenses are cylindrical lenses, a direction in which an incident area of the laser beam has a curvature in the cylindrical lens of one of the lens arrays is orthogonal to a direction in which an incident area of the laser beam has curvature in the cylindrical lens of the other lens array, one of the lens arrays is rotated in a direction in which the incident area of the cylindrical lens thereof has the curvature, and the other lens array is also rotated in a direction in which the incident area of the cylindrical lens thereof has the curvature.

7. The inspection apparatus according to claim 5, wherein the two lens arrays differ from each other in a rotating speed, and a time necessary for the lens array having the slower rotating speed to make one completion rotation is matched with an imaging time of the image sensor.

8. The inspection apparatus according to claim 7, wherein the rotating speed of one of the two lens arrays is not an integral multiple of the rotating speed of the other lens array.

9. The inspection apparatus according to claim 5, wherein the standard image is a reference image produced from design data of the pattern.

10. An inspection apparatus comprising:

an illumination apparatus for illuminating a sample of an inspection target with light, comprising a light source that emits a laser beam, and two lens arrays to which the laser beam is illuminated, a plurality of element lenses, each element lens having a diameter greater than or equal to that of the laser beam, arranged in the lens arrays, the lens arrays being rotatable through an optical axis of the laser beam;

an optical image acquiring unit that causes the light transmitted through the sample to be illuminated on an image sensor to acquire an optical image of the sample; and a comparison circuit that compares one or a plurality of pixels concerned in the optical image to the surrounding pixels to detect a defect, wherein the two lens arrays are arrayed in an optical axis direction of the laser beam, and the element lenses in each lens array are arranged such that boundary between the element lenses adjacent to each other radiates from a rotation center of the lens array and such that a direction in which the element lens of one of the lens arrays traverses the optical axis of the laser beam is orthogonal to a direction in which the element lens of the other lens array traverses the optical axis of the laser beam.

11. The inspection apparatus according to claim 10, wherein each of the element lenses are cylindrical lenses, a direction in which an incident area of the laser beam has a curvature in the cylindrical lens of one of the lens arrays is orthogonal to a direction in which an incident area of the laser beam has curvature in the cylindrical lens of the other lens array, one of the lens arrays is rotated in a direction in which the incident area of the cylindrical lens thereof has the curvature, and the other lens array is also rotated in a direction in which the incident area of the cylindrical lens thereof has the curvature.

12. The inspection apparatus according to claim 10, wherein the two lens arrays differ from each other in a rotating speed, and a time necessary for the lens array having the slower rotating speed to make one completion rotation is matched with an imaging time of the image sensor.

13. The inspection apparatus according to claim 12, wherein the rotating speed of one of the two lens arrays is not an integral multiple of the rotating speed of the other lens array.

* * * * *